United States Patent
Omura

(10) Patent No.: US 9,084,582 B2
(45) Date of Patent: Jul. 21, 2015

(54) RADIATION IMAGING APPARATUS AND METHOD OF CONTROLLING RADIATION IMAGING APPARATUS

(71) Applicant: CANON KABUSHIKI KAISHA, Tokyo (JP)

(72) Inventor: Satoru Omura, Chigasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 96 days.

(21) Appl. No.: 14/037,503

(22) Filed: Sep. 26, 2013

(65) Prior Publication Data

US 2014/0093046 A1 Apr. 3, 2014

(30) Foreign Application Priority Data

Sep. 28, 2012 (JP) ................. 2012-218460

(51) Int. Cl.
*A61B 6/00* (2006.01)

(52) U.S. Cl.
CPC ............... *A61B 6/547* (2013.01); *A61B 6/4405* (2013.01); *A61B 6/462* (2013.01)

(58) Field of Classification Search
CPC ...... A61B 6/4405; A61B 6/462; A61B 6/465; A61B 2019/025; A61B 2560/0437; A61B 6/00; A61B 6/44; A61B 6/547; H05G 1/02; G21K 5/00
See application file for complete search history.

(56) References Cited

U.S. PATENT DOCUMENTS

| | | | | |
|---|---|---|---|---|
| 3,790,805 | A * | 2/1974 | Foderaro | 378/198 |
| 4,341,279 | A * | 7/1982 | Waerve | 180/19.2 |
| 4,387,468 | A * | 6/1983 | Fenne et al. | 378/198 |
| 4,752,948 | A * | 6/1988 | MacMahon | 378/198 |
| 5,067,145 | A * | 11/1991 | Siczek et al. | 378/198 |
| 5,081,662 | A * | 1/1992 | Warden et al. | 378/198 |
| 5,425,069 | A * | 6/1995 | Pellegrino et al. | 378/198 |
| 5,586,162 | A * | 12/1996 | Grichnik | 378/198 |
| 5,712,482 | A * | 1/1998 | Gaiser et al. | 250/363.08 |
| 6,193,415 | B1 * | 2/2001 | Kadowaki et al. | 378/198 |
| 6,237,707 | B1 * | 5/2001 | Lyke et al. | 180/19.3 |
| 7,309,159 | B2 * | 12/2007 | Watanabe | 378/198 |
| 7,643,613 | B2 | 1/2010 | Watanabe | |
| 8,474,835 | B1 * | 7/2013 | Rossi | 280/47.35 |
| 8,568,028 | B2 * | 10/2013 | Wendlandt et al. | 378/198 |
| 8,672,543 | B2 * | 3/2014 | Kralles et al. | 378/198 |
| 8,849,370 | B2 * | 9/2014 | Bouvier | 600/407 |
| 8,876,379 | B2 * | 11/2014 | DiRisio et al. | 378/198 |
| 2003/0190014 | A1 * | 10/2003 | Nakagawa et al. | 378/193 |
| 2006/0253022 | A1 * | 11/2006 | Omernick et al. | 600/425 |

(Continued)

FOREIGN PATENT DOCUMENTS

| | | |
|---|---|---|
| JP | 2006-081690 A | 3/2006 |
| JP | 2006-158508 A | 6/2006 |

(Continued)

*Primary Examiner* — Michael Logie
(74) *Attorney, Agent, or Firm* — Carter, DeLuca, Farrell & Schmidt, LLP

(57) ABSTRACT

A radiation imaging apparatus includes an irradiation unit configured to irradiate radiation, a positioning unit configured to position the irradiation unit, and a cart unit configured to move while the irradiation unit and the positioning unit are mounted on the cart unit. The radiation imaging apparatus includes a moving unit configured to hold a display unit below the irradiation unit and to slide the display unit along a display screen of the display unit outwardly from the cart unit.

18 Claims, 16 Drawing Sheets

(56) References Cited

U.S. PATENT DOCUMENTS

| | | | |
|---|---|---|---|
| 2008/0081992 A1* | 4/2008 | Kagermeier | 600/425 |
| 2009/0046463 A1* | 2/2009 | Coombs et al. | 362/253 |
| 2010/0002844 A1* | 1/2010 | Van Woezik | 378/204 |
| 2010/0329426 A1* | 12/2010 | Oda et al. | 378/98.2 |
| 2010/0329427 A1* | 12/2010 | Takae et al. | 378/98.5 |
| 2011/0110496 A1* | 5/2011 | Foos et al. | 378/98.5 |
| 2011/0110498 A1* | 5/2011 | Takae et al. | 378/102 |
| 2011/0198460 A1* | 8/2011 | Stifal et al. | 248/201 |
| 2011/0291800 A1* | 12/2011 | Butzine et al. | 340/8.1 |
| 2012/0093298 A1* | 4/2012 | Lalena | 378/198 |
| 2013/0039473 A1* | 2/2013 | Kojima | 378/91 |
| 2013/0064351 A1* | 3/2013 | Urbon et al. | 378/98.5 |
| 2013/0129048 A1* | 5/2013 | Chicchetti et al. | 378/62 |
| 2013/0266122 A1* | 10/2013 | Patil et al. | 378/98 |
| 2013/0272499 A1* | 10/2013 | Simmons et al. | 378/62 |

FOREIGN PATENT DOCUMENTS

| | | |
|---|---|---|
| JP | 2007-313252 A | 12/2007 |
| JP | 2009-183368 A | 8/2009 |
| JP | 2010-051745 A | 3/2010 |

* cited by examiner

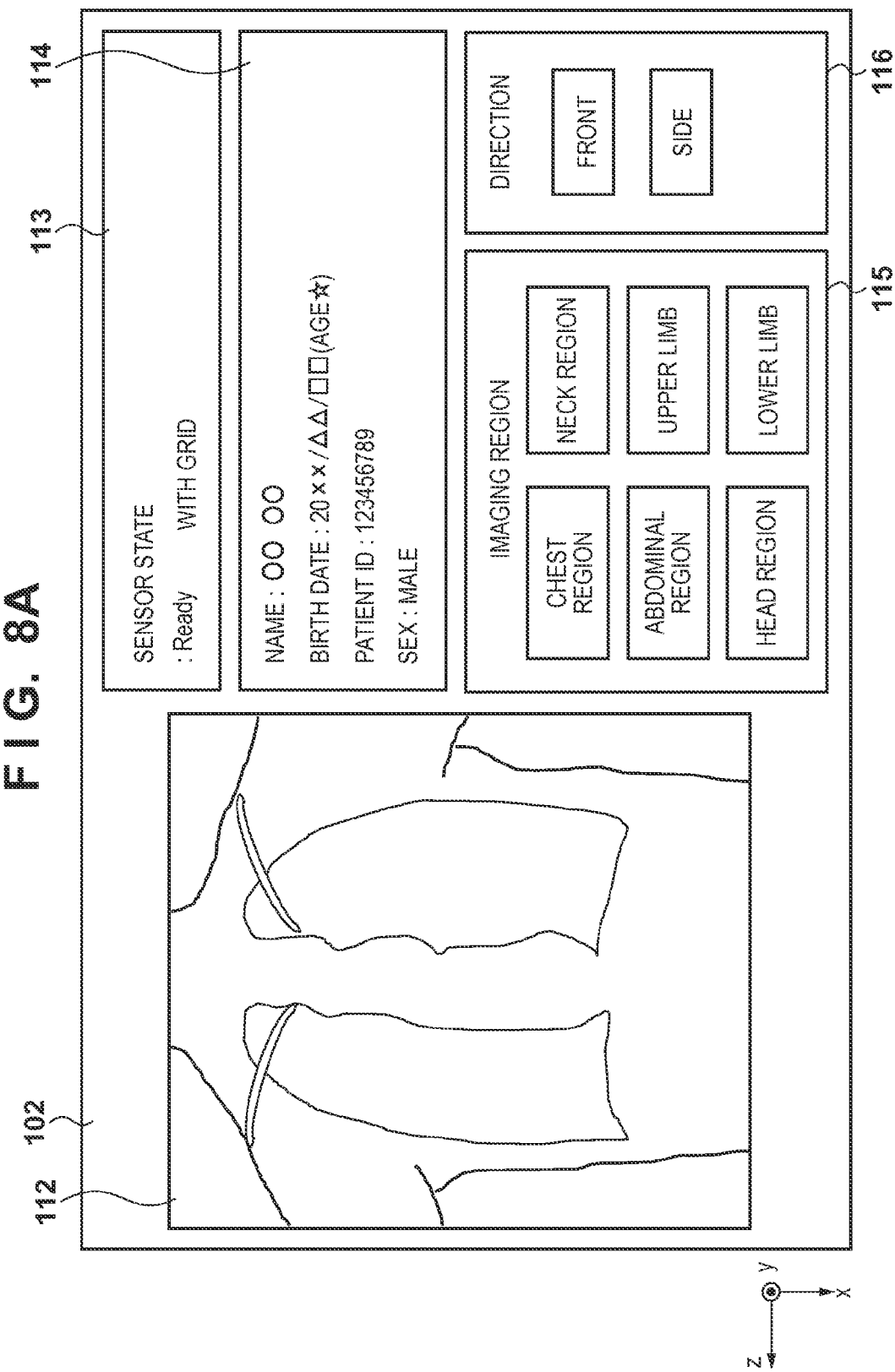

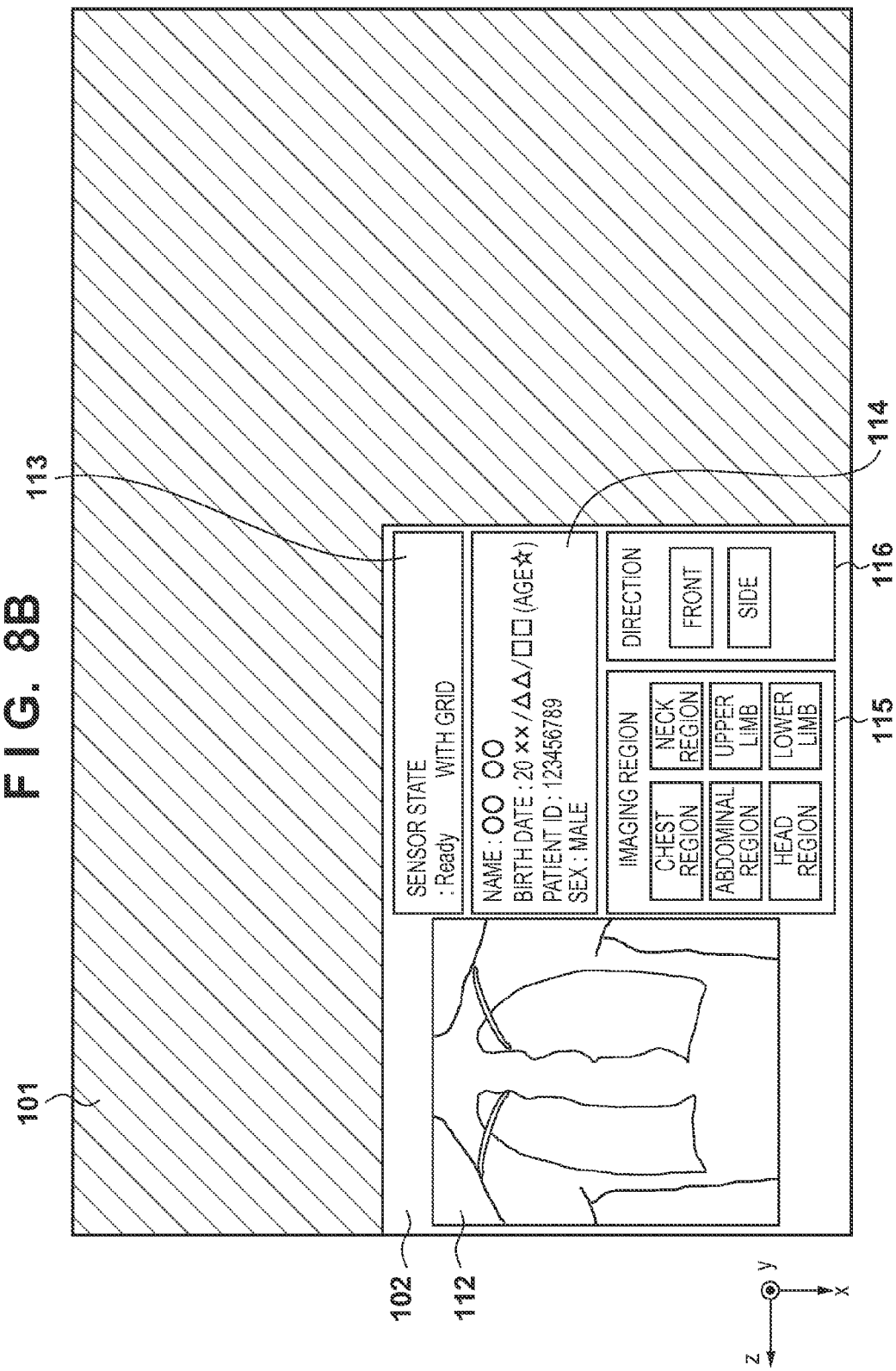

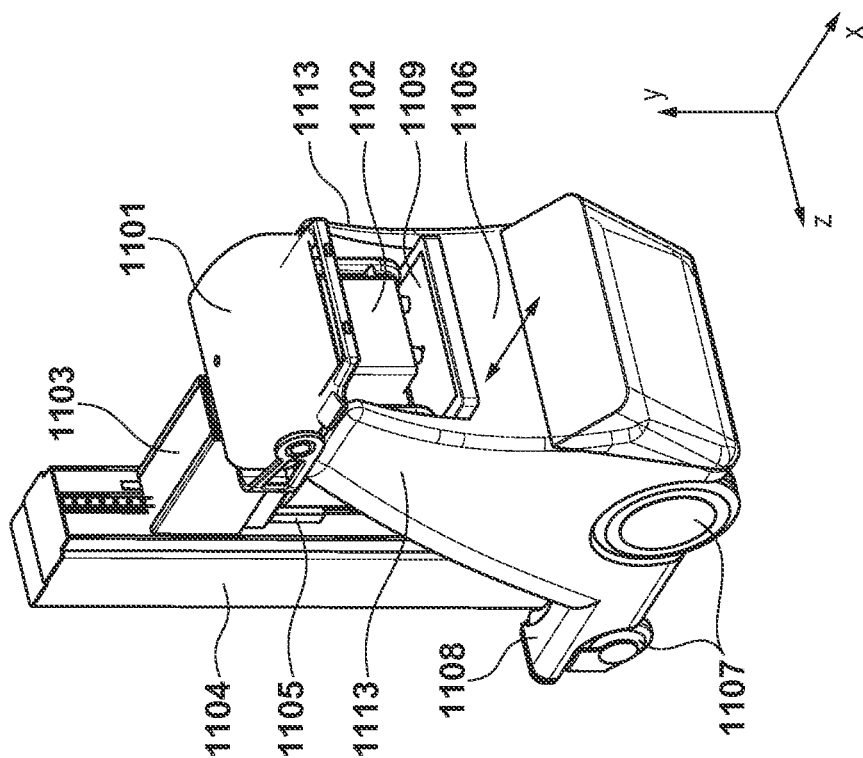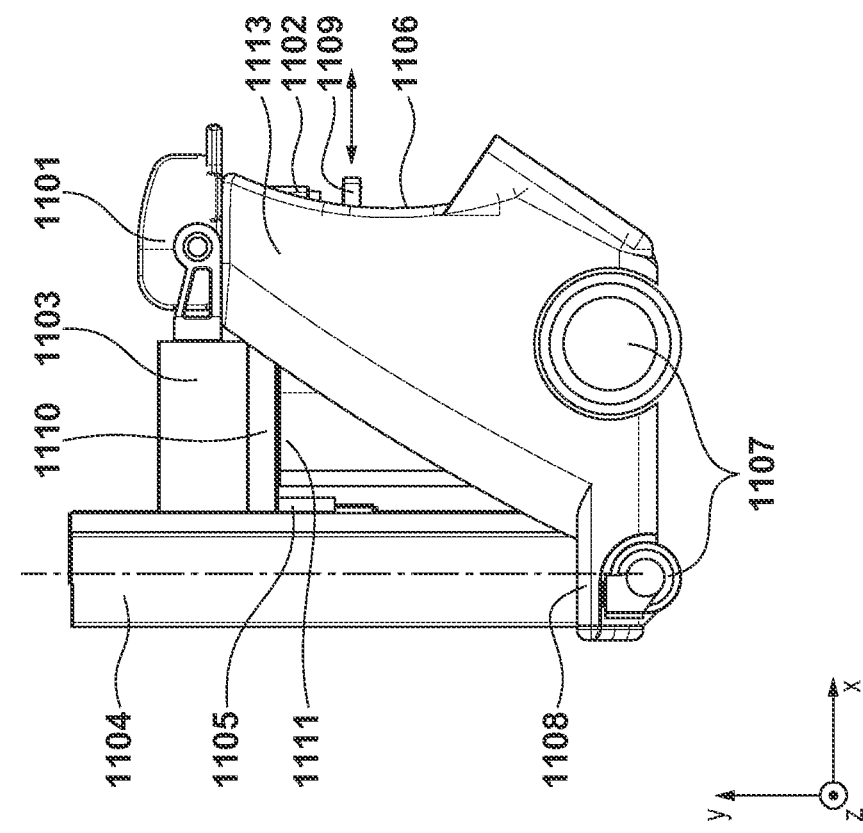

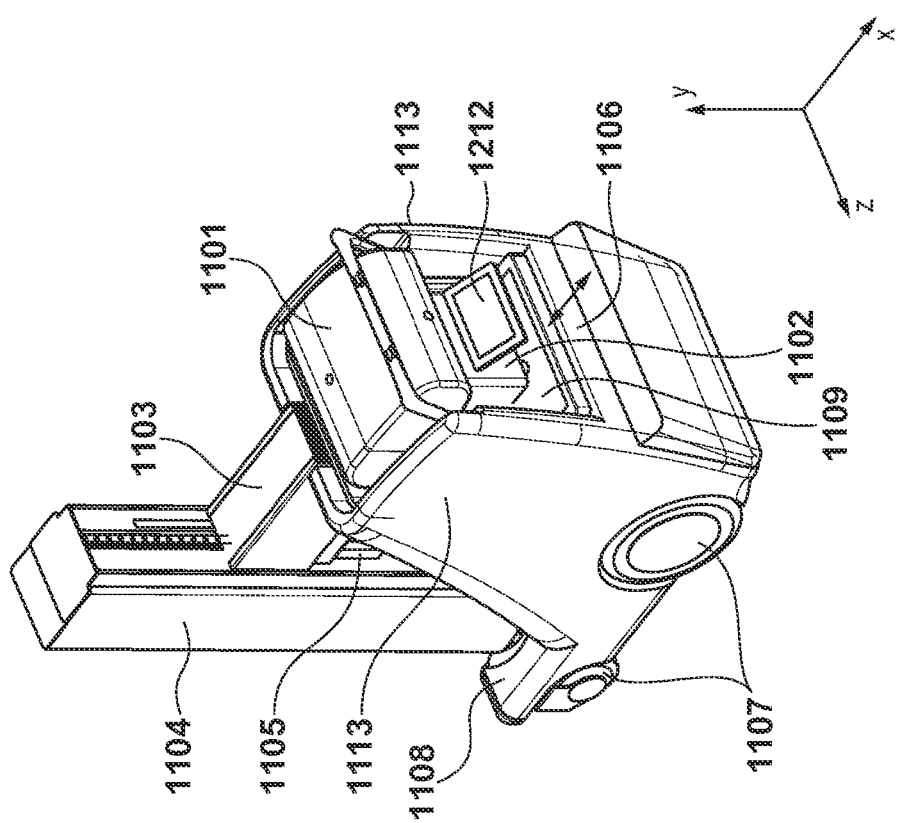
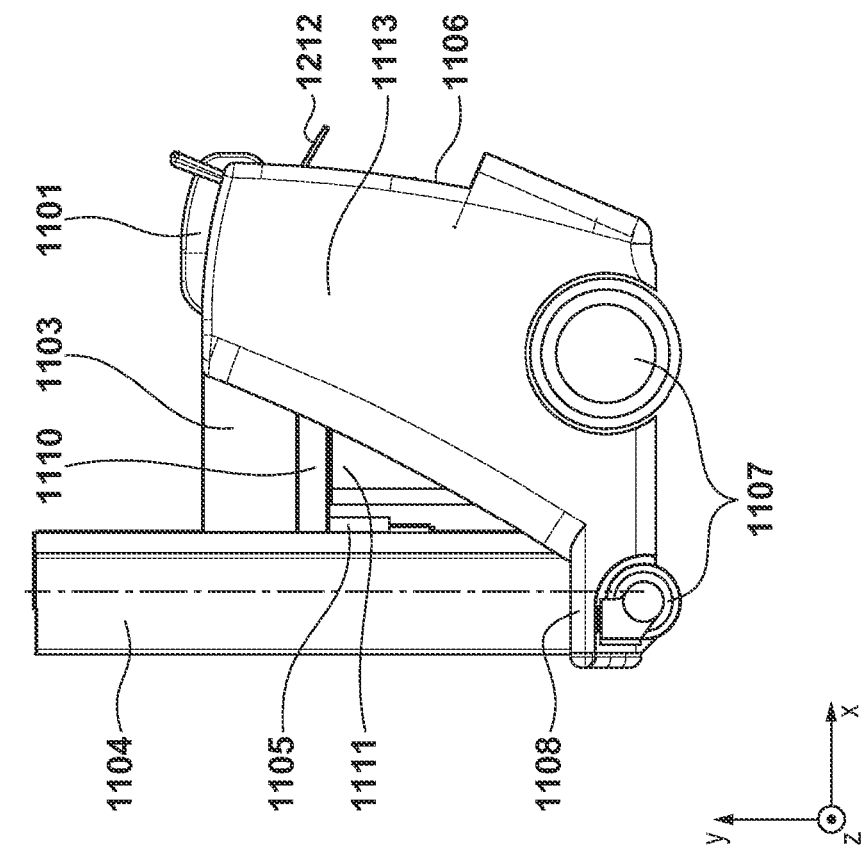

RADIATION IMAGING APPARATUS AND METHOD OF CONTROLLING RADIATION IMAGING APPARATUS

BACKGROUND OF THE INVENTION

1. Field of the Invention

The present invention relates to a radiation imaging apparatus for obtaining a radiation image from radiation transmitted through an object and a method of controlling the radiation imaging apparatus.

2. Description of the Related Art recently, as medical X-ray imaging apparatuses, there have been widely used a movable X-ray imaging cart which performs X-rays imaging in a hospital room or operating room and an apparatus which holds an X-ray tube by using a C-arm and detects X-rays transmitted through a patient by irradiating the patient with X-rays from the X-ray tube.

When performing X-ray imaging by using the movable X-ray imaging cars, it is necessary to use an arrangement for changing the position of an X-ray tube on a bed to place the X-ray tube above an object lying on the bed. When imaging the four limbs of the object, in particular, it is impossible to keep properly positioning an X-ray detector and an X-ray tube and to capture a proper image unless it is possible to place the X-ray tube at any position on the bed.

In addition, the movable X-ray imaging cart runs through the narrow space between beds in a hospital room and on corridors between hospital wards along which stretchers and other medical apparatuses come and go, and hence needs to be folded into a compact structure at the time of movement. For this purpose, this apparatus needs to be configured such that the boom holding the X-ray tube can be accommodated in small size at the time of movement, and the X-ray tube can be widely spread out so as to be positioned at a proper position relative to the X-ray detector at the time of X-ray imaging on an object in accordance with an imaging region of the object.

Japanese Patent Laid-Open No. 2006-81690 discloses an arrangement configured to make a boom which supports an X-ray tube extensible to as to extend the boom at the time of X-ray imaging and contract the boom for accommodation at the time of movement.

The operator moves the movable X-ray imaging cart while checking the information and position of the patient to be imaged next which are displayed on the monitor installed on a moving cart unit at the time of doctor's round, thereby implementing smooth doctor's round. However, when using the X-ray imaging apparatus disclosed in Japanese Patent Laid-Open No. 2006-81690, since the X-ray tube is placed near the monitor at the time of movement, the operator cannot check the monitor at the time of movement.

The present invention therefore proves a radiation imaging apparatus which allows the operator to check the information displayed on a display unit at the time of movement and is excellent in operability.

SUMMARY OF THE INVENTION

According to one aspect of the present invention, there is provided a radiation imaging apparatus having an irradiation unit configured to irradiate radiation, a positioning unit configured to position the irradiation unit, and a cart unit configured to move while the irradiation unit and the positioning unit are mounted on the cart unit, the radiation imaging apparatus comprising a moving unit configured to hold a display unit below the irradiation unit and to slide the display unit along a display screen of the display unit outwardly from the cart unit.

According to another aspect of the present invention, there is provided a method of controlling a radiation imaging apparatus having an irradiation unit configured to irradiate radiation, a position unit configured to position the irradiation unit, a cart unit configured to move whole the irradiation unit and the positioning unit are mounted on the cart unit, and a moving unit configured to hold a display unit below the irradiation unit and slide the display unit along a display screen of the display unit outwardly from the cart unit, the method comprising: an obtaining step of obtaining a relative positional relationship between the irradiation unit and the display unit based on a state of the positioning unit and a state of the moving unit; a specifying step of specifying a display are used for display on the display unit based on the positional relationship; and a display control step of displaying information associated with radiation imaging in the specified display area.

The present invention can provide a radiation imaging apparatus which allows the operator to check the information displayed on a display unit at the time of movement and is excellent in operability.

Further features of the present invention will become apparent from the following description of exemplary embodiments (with reference to the attached drawings).

BRIEF DESCRIPTION OF THE DRAWINGS

FIG. 8A is a view for explaining a monitor display when an X-ray tube is moved from the accommodation position in the second embodiment;

FIG. 8B is a view for explaining a monitor display when the X-ray tube is returned to the accommodation position in the second embodiment;

FIGS. 11A and 11B are views showing the arrangement of a radiation imaging apparatus according to the fourth embodiment;

FIGS. 12A and 12B are views showing the arrangement of a radiation imaging apparatus according to the fifth embodiment.

DESCRIPTION OF THE EMBODIMENTS

First Embodiment

Figure 1A:
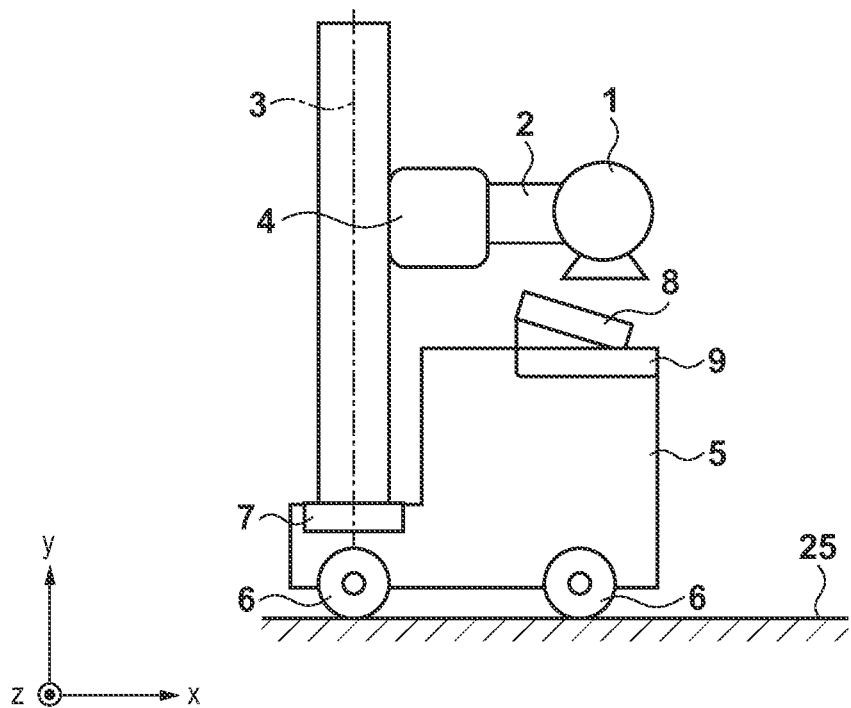
FIGS. 1A and 1B are views showing the arrangement of a radiation imaging apparatus according to the first embodiment.
Figure 1B:
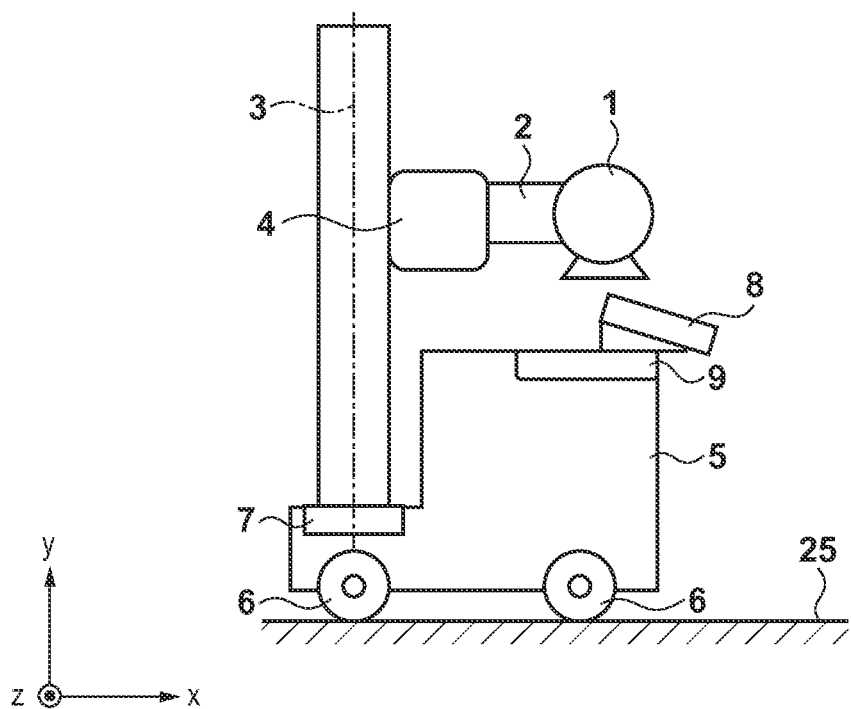
Figure 2A:
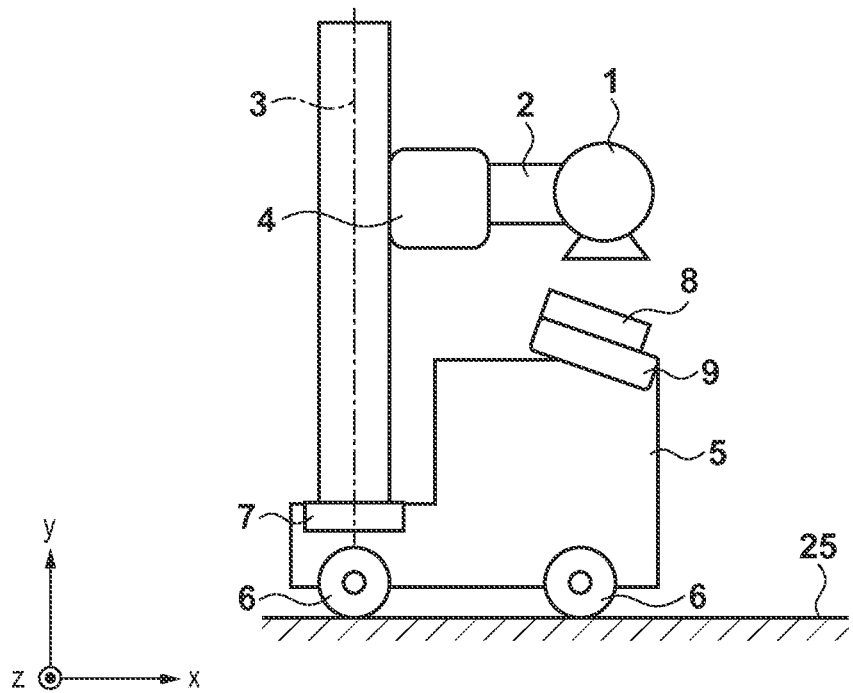
FIGS. 2A and 2B are views showing the arrangement of the radiation imaging apparatus according to the first embodiment.
Figure 2B:
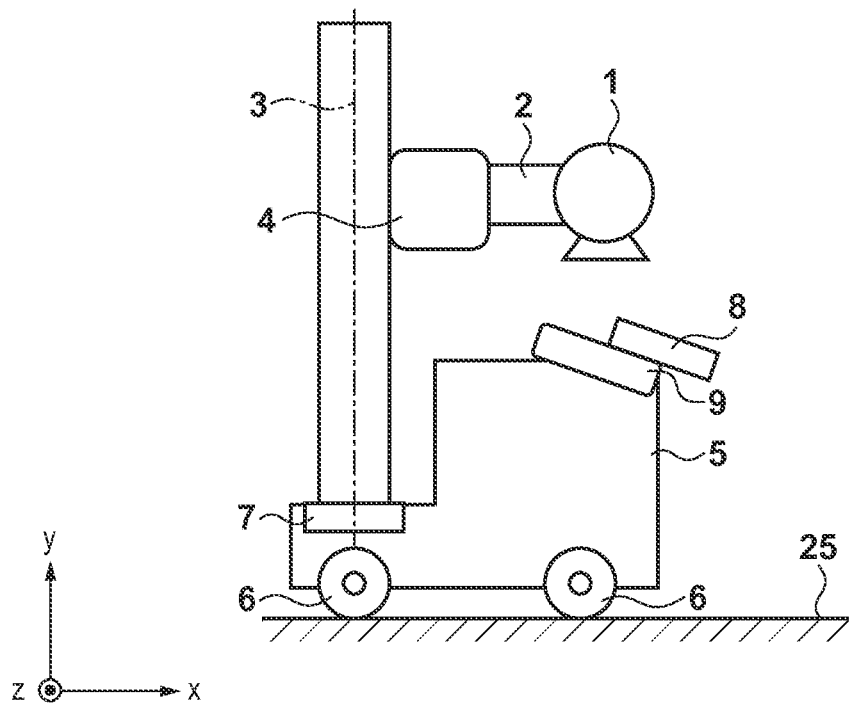

FIGS. 1A, 1B, 2A, and 2B are views showing the arrangement of a radiation imaging apparatus (to be referred to as a movable X-ray imaging apparatus) according to the first embodiment. FIGS. 1A and 2A show a state in which a monitor 8 of the apparatus is accommodated. FIGS. 1B and 2B show a state in which the monitor of the apparatus is slid/moved in the horizontal direction (x direction). FIG. 3B is a block diagram showing the functional arrangement of a radiation imaging apparatus (movable X-ray imaging apparatus) according to the first embodiment. The functional arrangement shown in FIG. 3B remains the same in the second and third embodiments described later.

Referring to FIGS. 1A, 1B, 2A, and 2B, an X-ray tube 1 irradiates radiation (X-rays). The X-ray tube 1 functions as an irradiation unit which irradiates radiation (X-rays). A boom 2 supports the X-ray tube 1 and includes an extensible portion which moves the X-ray tube 1 in at least the horizontal direction (x direction) and an extension/contraction position fixing portion which fixes (holds) the position of the X-ray tube 1 at the moving position of the X-ray tube 1. A column 3 supports the boom 2. A boom support unit 4 connects the boom 2 to the column 3, and includes a vertical moving portion which can move the boom 2 in the vertical direction (y direction) along the column 3 and a moving position fixing portion which can fix the boom 2 at an arbitrary position on the column 3 upon movement. The boom 2, the boom support unit 4 and the column 3 functions as a positioning unit 35 which positions the X-ray tube 1.

A cart unit 5 supports the column 3. The cart unit 5 supports the X-ray tube 1 through the boom 2, the boom support unit 4, and the column 3. The cart unit 5 can move while the X-ray tube 1, the boom 2, the boom support unit 4, and the column 3 are mounted on the cart unit. A moving mechanism 6 is a mechanism which allows the cart unit 5 to move by rotating while, for example, a plurality of tires or casters are placed on a ground 25.

A column rotating unit 7 connects the cart unit 5 to the column 3 and includes a rotating member (for example, a bearing) at the connecting portion between the cart unit 5 and the column 3 to support the column 3 on the cart unit 5 so as to allow the column 3 to rotate about an axis perpendicular to the ground 25. The column rotating unit 7 also includes, for example, a non-excitation brake (rotational position holding unit), and can stop the rotation of the column 3 at an arbitrary position by operating the non-excitation brake.

The monitor 8 (display unit) i installed on the upper surface of the cart unit 5 through a slide mechanical unit 9 (moving unit) (to be described later). The monitor 8 (display unit) displays the information and position of a patient to be imaged at the time of doctor's round and an examination information list. The operator can also operate the monitor 8 (display unit) to set imaging conditions and transmit a captured X-ray image to an intra-hospital network. In addition, the operator can perform login operation to give permission to operate or logout operation with respect to a control unit 504 in the apparatus, activate the apparatus, or perform shutdown operation for the apparatus via an operation window on the monitor 8 (display unit).

The slide mechanical unit 9 (moving unit) which moves (slides/moves) the monitor 8 in the horizontal direction (x direction) is provided between the cart unit 5 and the monitor 8. The slide mechanical unit 9 (moving unit) holds the monitor 8 (display unit) below the X-ray tube 1, and can slide/move the monitor 8 relative to the cart unit 5 and the X-ray tube 1.

The slide mechanical unit 9 is configured to slide/move the monitor 8 in the horizontal direction (x direction) in the case shown in FIGS. 1A and 1B and to slide/move the monitor 8 in an oblique direction (a direction inclined in the horizontal direction (x-axis direction)) in the case shown in FIGS. 2A and 2B. If, for example, the slide mechanical unit 9 is configured in the manner shown in FIGS. 2A and 2B, it is possible to ensure the distance between the X-ray tube 1 and the monitor 8 with a small slide amount as compared with the arrangement of the slide mechanical unit 9 in FIGS. 1A and 1B, thereby allowing the operator to easily make a visual check on the monitor 8.

Figure 3A:
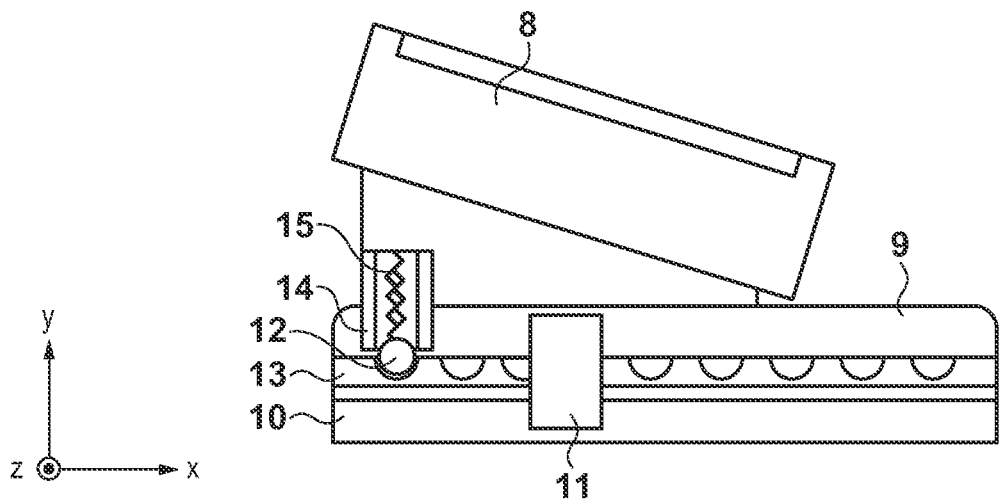
FIG. 3A is a view showing the arrangement of a slide mechanical unit in the first embodiment.
Figure 3B:
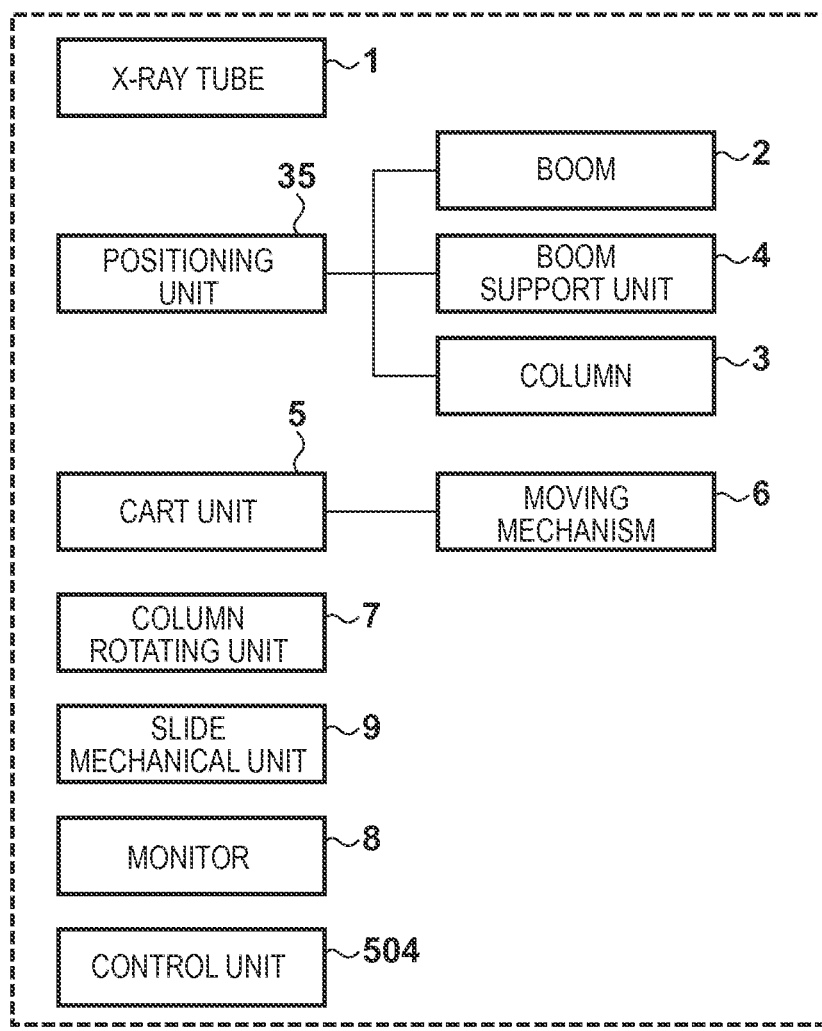
FIG. 3B is a block diagram showing the functional arrangement of the apparatus.

FIG. 3A is a view showing the concrete arrangement of the slide mechanical unit 9 (moving unit). The slide mechanical unit 9 includes, as constituent elements, a guide rail 10 and a block 11 which can move along the guide rail 10. The lower surface side of the guide rail 10 is fixed on the cart unit 5. The block 11 can move along the guide rail 10. The upper portion of the block 11 is connected/fixed to the monitor 8. This allows the monitor 8 to move in a direction along the guide rails 10 through the block 11 to which the monitor 8 is fixed/connected.

A roller guide 14 and an elastic member 15 (for example, a compression spring) hold a spherical roller 12 while part of the roller 12 protrudes from the lower surface of the roller guide 14. A through hole having a larger diameter than the roller 12 is formed in the roller guide 14. The elastic member 15 (for example, a compression spring) is provided in the through hole of the roller guide 14. One end of the elastic member 15 (compression spring) is fixed to the lower surface side of the monitor 8. The other end of the elastic member 15 is attached to the roller 12.

The elastic member 15 (compression spring) biases the roller 12 toward the guide rail 10 (in the −y direction). When the roller 12 is moved inside the through hole of the roller guide 14 and pushed upward (in the +y direction), the repulsive force of the elastic member 15 compressed to raise the roller 12 acts to push back the roller 12 downward (in the −y direction). The roller 12, the roller guide 14, and the elastic member 15 are configured to move together with the monitor 8 when it moves along the guide rail 10. A stopper plate 13 is provided on the guide rail 10 and has a plurality of dented portions, in which the roller 12 is fitted, at arbitrary intervals on the moving orbit of the roller 12. The slide mechanical unit 9 (moving unit) functions as a moving unit for moving the monitor 8 relative to the cart unit 5.

When the monitor 8 slides/moves, the roller 12 is fitted in a dented portion of the stopper plate 13. This can stop the movement of the monitor 8 at an arbitrary position on the guide rail 10. As shown in FIGS. 2A and 2B, when the monitor 8 moves in an oblique direction, the force required to stop the movement of the monitor 8 is larger than that in FIGS. 1A and 1B. However, it is possible to cope with this situation by changing the shape of each dented portion of the stopper plate 13 or elastic member 15 (compression spring). In the slide mechanical unit 9 (moving unit), the roller 12, the roller guide 14, the elastic member 15 (compression spring), and the stopper plate 13 function as a position holding unit which holds the moving position of the monitor 8 (display unit).

According to this embodiment, since the cart unit can move in the horizontal direction and oblique directions relative to the cart unit, the operator can check the information displayed on the monitor even if the X-ray tube is placed above the monitor at the time of movement. In addition, this can improve the operability for the operator.

Second Embodiment

Figure 4:
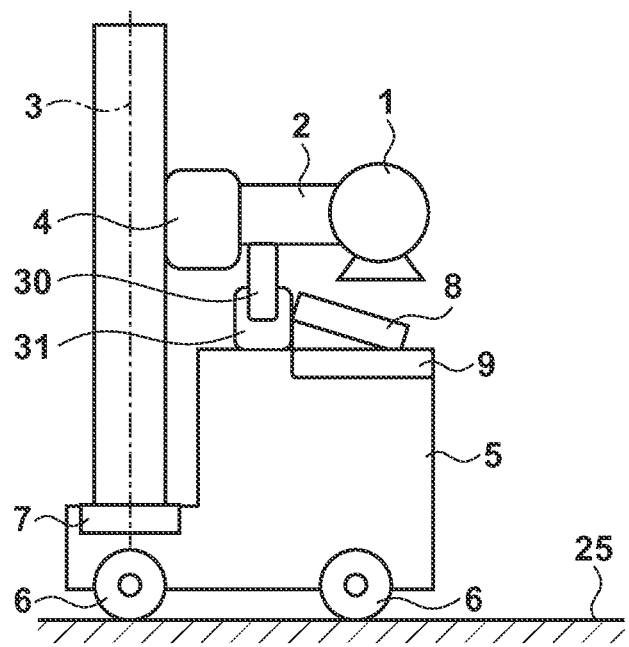
FIG. 4 is a view showing the arrangement of a radiation imaging apparatus according to the second embodiment.

FIG. 4 is a view showing the arrangement of the radiation imaging apparatus (movable X-ray imaging apparatus) according to the second embodiment. In addition to the arrangement of the movable X-ray imaging apparatus according to the first embodiment, the second embodiment includes an arrangement (FIG. 5B) for detecting and controlling the position of the monitor 8 and the arrangement (FIG. 4) constituted by an accommodation rod 30 for guiding a boom 2 and an X-ray tube 1 into an accommodated state at the time of the movement of the apparatus and an accommodation rod receiving unit 31 instead of the movable X-ray imaging apparatus according to the first embodiment. Referring to FIG. 4, the components ranging from the X-ray tube 1 to a monitor 8 are the same as those in the first embodiment described with reference to FIGS. 1A, 1B, 2A, and 2B.

The accommodation rod 30 protrudes downward from the boom 2 in the vertical direction (−y direction). The accommodation rod receiving unit 31 is installed on the cart unit 5. Fitting the accommodation rod 30 in the accommodation rod receiving unit 31 will guide the boom 2 and the X-ray tube 1 to the accommodation positions at the time of the movement of the apparatus. The accommodation rod 30 or the accommodation rod receiving unit 31 is provided with a contact sensor 505 (FIG. 5B) for detecting that they fit in each other. The contact sensor 505 functions as an accommodated state detection unit which detects whether the X-ray tube 1 (irradiation unit) is accommodated at the accommodation position. The detection result obtained by the contact sensor 505 is input to a control unit 504 which controls the overall operation of the apparatus. When a signal indicating the detection result from the contact sensor 505 is input to the control unit 504, the control unit 504 determines that the accommodation rod 30 is fitted in the accommodation rod receiving unit 31.

Figure 5A:
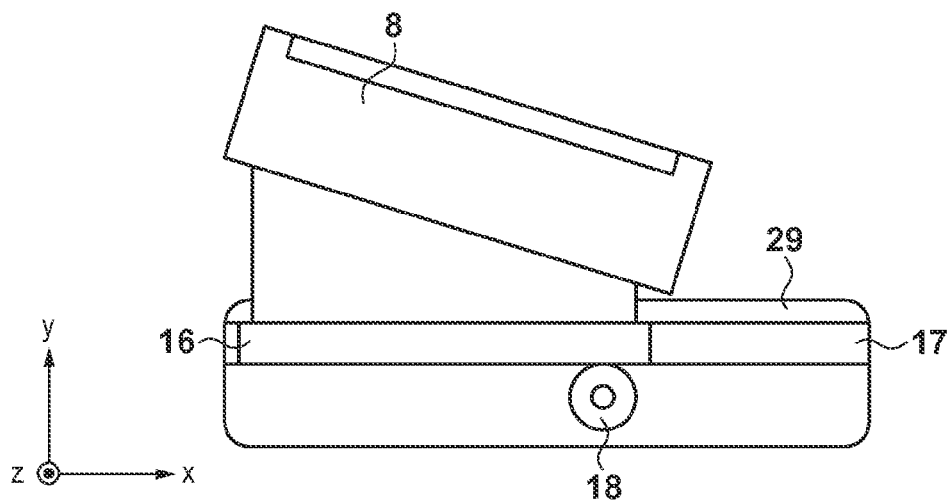
FIG. 5A is a view showing the arrangement of a slide mechanical unit in the second embodiment.
Figure 5B:
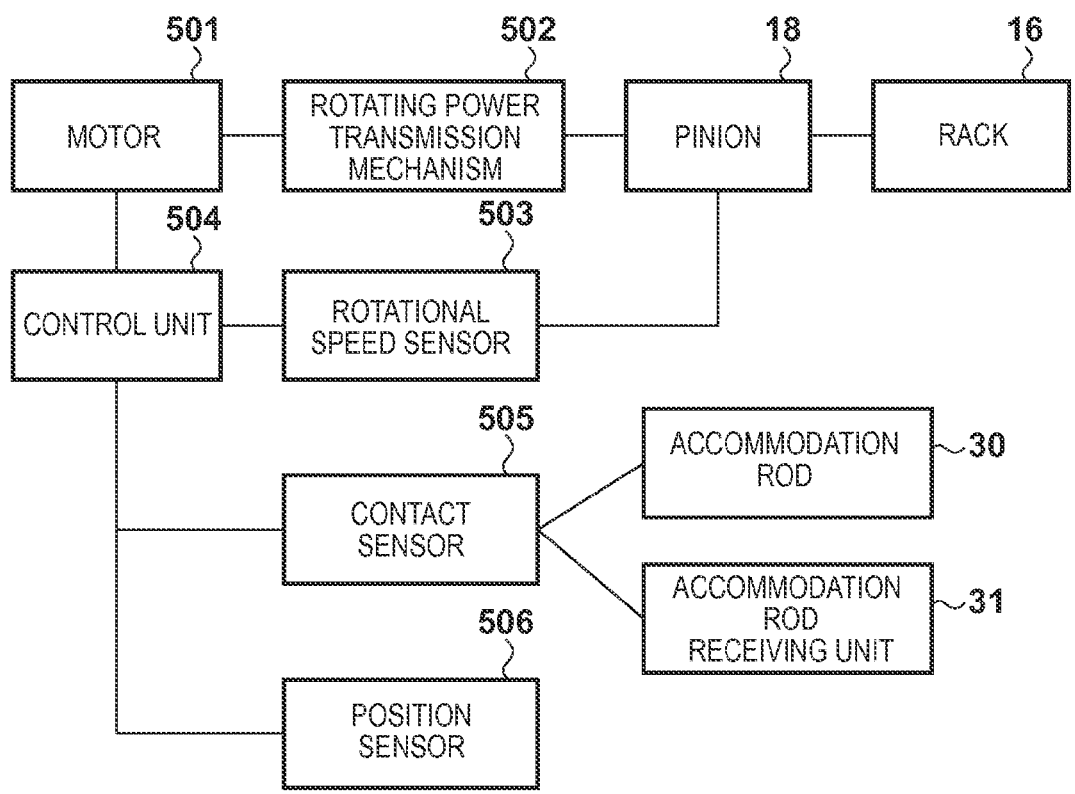
FIG. 5B is a block diagram showing the arrangement of the control system of the radiation imaging apparatus.

FIG. 5A shows the concrete arrangement of a slide mechanical unit 29 in a movable X-ray imaging apparatus according to the second embodiment. A side surface inside the slide mechanical unit 29 is provided with a groove portion 17 which guides the movement of a rack 16. FIG. 5B shows a functional arrangement for detecting and controlling the position of the monitor 8. A motor 501 (generation unit) generates a driving force for moving the monitor 8. A rotating power transmission mechanism 502 transmits the rotating power of the motor 501. A pinion 18 (rotary drive mechanism) rotates in accordance with the transmitted rotating power. A rotational speed sensor 503 detects the rotational speed of the pinion 18 (rotary drive mechanism). The detection result obtained by the rotational speed sensor 503 is input (fed back) to the control unit 504. The rotational speed sensor 503 functions as a movement detection unit which detects the movement (moving amount) of the slide mechanical unit 29.

The control unit 504 controls the rotation of the motor 501 in accordance with the detection result obtained by the rotational speed sensor 503. The rack 16 (linear moving mechanism) converts the rotary drive of the pinion 18 into linear movement and linearly moves along the groove portion 17. The monitor 8 is provided on the rack 16. The control unit 504 can linearly move the rack 16 and control the movement of the monitor 8 to an arbitrary position in the x direction by controlling the rotation of the motor 501 in accordance with the detection result obtained by the rotational speed sensor 503. The control unit 504 detects the position of the monitor 8 from the detection result obtained by the rotational speed sensor 503 and the linear moving amount of the rack 16. This allow the control unit 504 to automatically change the position of the monitor 8 while grasping the position of the monitor 8. Releasing the brake of the motor 501 allows the operator to manually change the position of the monitor 8.

In addition, the control unit 504 can perform control to release the brake (lock) of the motor 501 upon detecting the contact between the accommodation rod 30 and the accommodation rod receiving unit 31 from the detection result obtained by the contact sensor 505. This makes it possible to manually move the monitor 8 only when the X-ray tube 1 is at the accommodation position. Alternatively, the control unit 501 may move the monitor 8 to an arbitrary position depending on whether the control unit 504 detects the contact between the accommodation rod 30 and the accommodation rod receiving unit 31 based on the detection result obtained by the contact sensor 505. For example, upon detecting no contact between the accommodation rod 30 and the accommodation rod receiving unit 31, the control unit 504 can control the slide moving mechanism so as to slide/move the monitor 8 from the outside of the upper surface of the cart unit 5 toward the inside. In addition, upon detecting the contact between the accommodation rod 30 and the accommodation rod receiving unit 31, the control unit 504 can control the slide moving mechanism so as to slide/move the monitor 8 from the inside of the upper surface of the cart unit 5 to the outside. This prevents the situation in which the operator cannot visually check anything on the monitor 8 when the X-ray tube 1 is accommodated. In addition, this prevents the monitor 8 from protruding from the apparatus when using the X-ray tube 1. This is, the operator need not perform much moving operation for the monitor 8, resulting in an improvement in operability.

Figure 10:
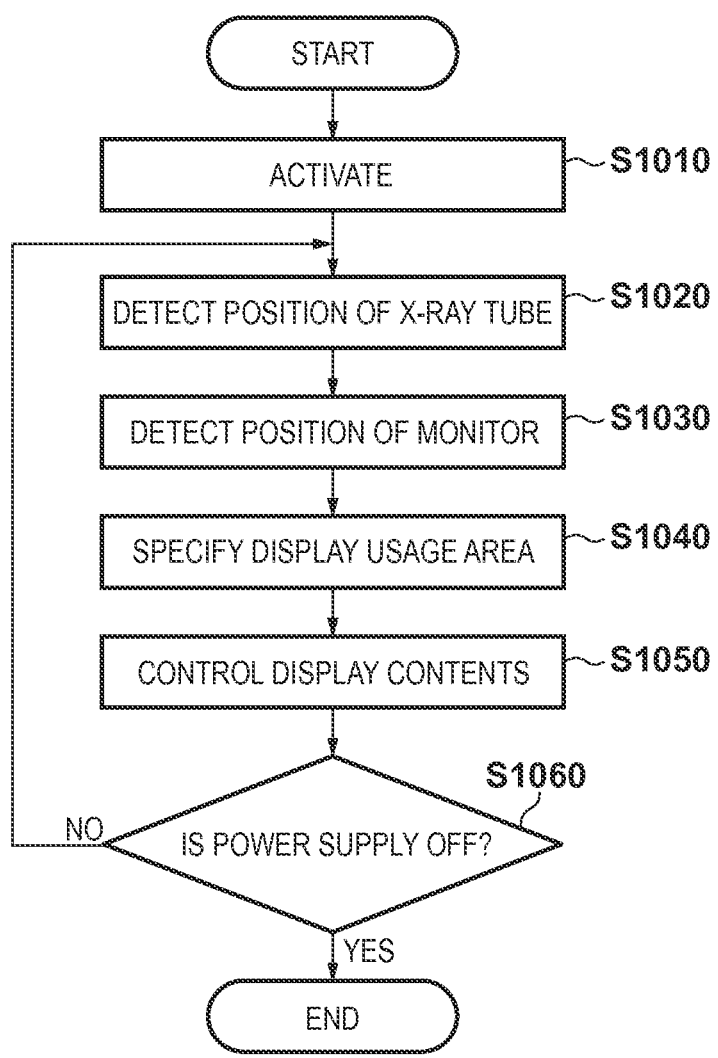
FIG. 10 is a flowchart for explaining a procedure for processing by a control unit.

FIG. 10 is a flowchart for explaining a procedure for processing by the control unit 504. First of all, the operator activates the control unit 504 by turning on the power supply (step S1010). In step S1020, the control unit 504 detects the position of the X-ray tube 1. In step S1030, the control unit 504 detects the position of the monitor 8. The control unit 504 can detect the relative positional relationship between the X-ray tube 1 and the monitor 8 by using the detection results obtained by the contact sensor 505 and an absolute position sensor 506. Note that the execution order of steps S1020 and S1030 is not limited to this processing procedure, and step S1030 may be executed before the execution of step S1020.

In step S1040, the control unit 504 specifies a display usage area 102 of the monitor 8 by using the position detection results on the X-ray tube 1 and the monitor 8 (the relative positional relationship between the X-ray tube 1 and the monitor 8). When, for example, the relative positional relationship between the X-ray tube 1 and the monitor 8 has changed upon movement of the monitor 8, the control unit 504 specifies a display usage area in accordance with this changed relative position. The control unit 504 has a table associating the position of the monitor 8 with the display area which can be visually checked by the operator, and can specify a display usage area by referring to the table. Display examples of the display usage area using this table will be described in detail later.

In step S1050, the control unit 504 controls display contents (for example, a display position, display size, and display items) displayed in the display usage area specified in step S1040. IN step S1060, the control unit 504 determines whether the power supply is OFF. If the power supply is OFF (YES in steps S1060), the control unit 504 terminates the processing. Upon determine in step S1060 that the power supply is not OFF (NO in step S1060), the process returns to step S1020 to repeat the same processing.

Figure 6A:
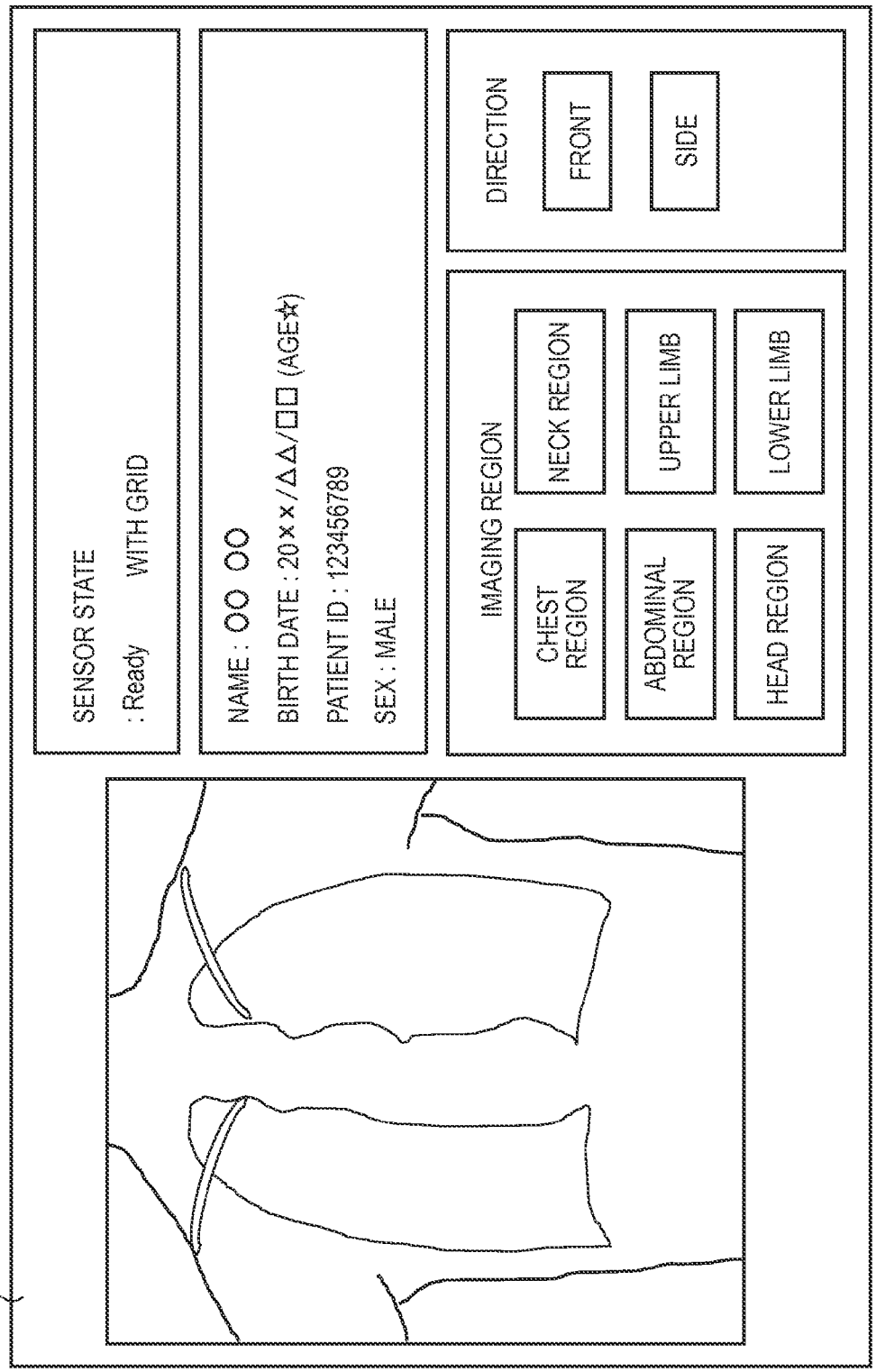
FIGS. 6A and 6B are views for explaining monitor displays in the second embodiment.
Figure 6B:
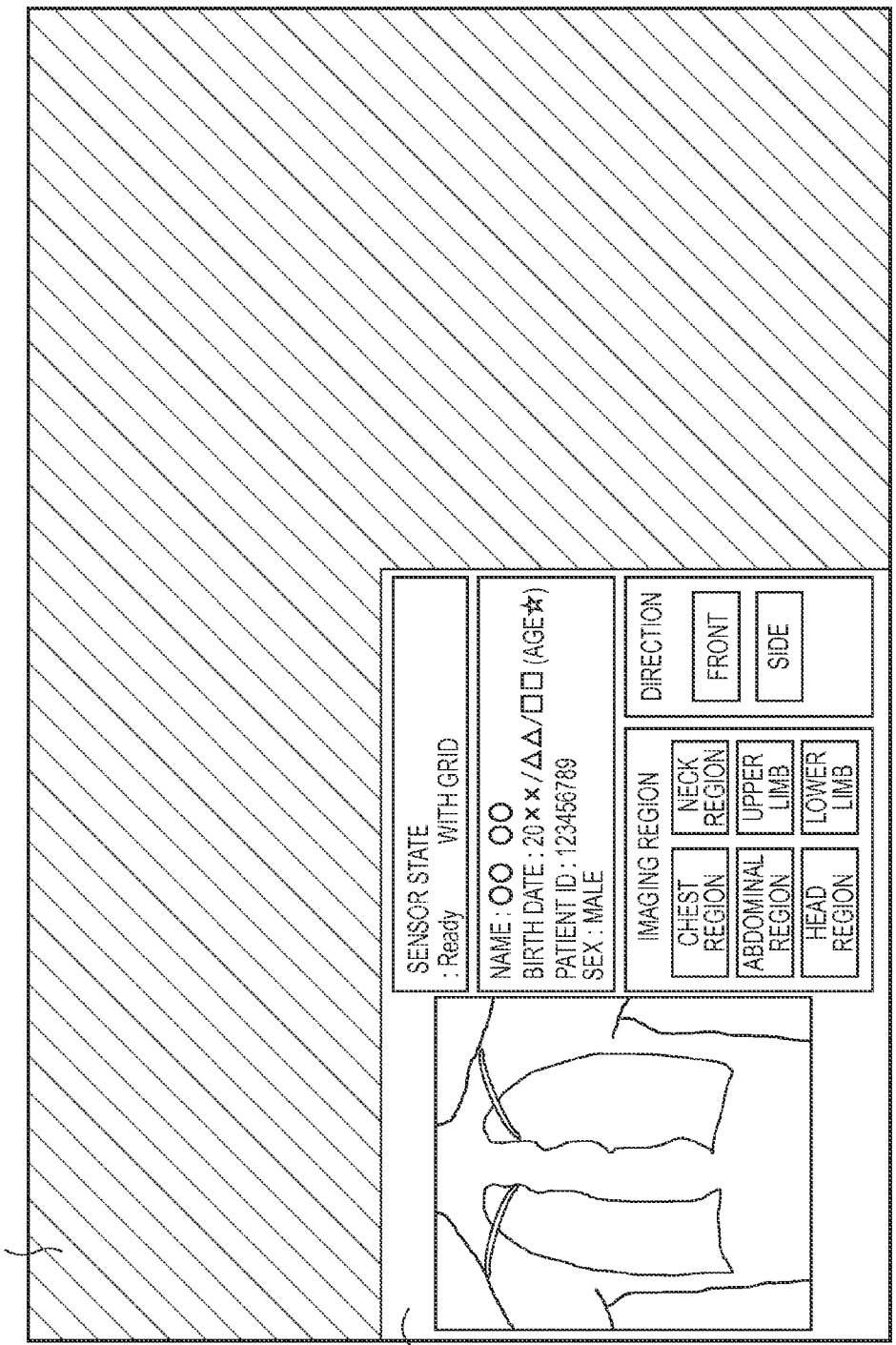

Display examples on the monitor 8 based on the processing in steps S1040 and S1050 will be described next. FIGS. 6A and 6B are views for explaining display on the monitor 8. FIG. 6A shows a general monitor display state. FIG. 6B shows a monitor display state in the process of sliding/moving the monitor 8. The second embodiment gives consideration to a state (at the time of movement of the apparatus) in which the X-ray tube 1 is at the accommodation position. Referring to FIG. 6B, and area 101 on the monitor 8 is an area which is not used for display, whereas the display usage area 102 is an area which is used for display on the monitor 8. Combining the areas 101 and 102 will form the monitor display enable range if the monitor 8. In the general state in FIG. 6A, the entire monitor display enable range is the display usage area 102. The control unit 504 has a table associating the position calculation result (position information) concerning the monitor 8 and the display area which can be visually checked by the operator. The control unit 504 changes the display (display position and display size) of the display usage area 102 on the monitor 8 in accordance with a change in the position of the monitor 8 by referring to the table. Note that the control unit 504 can obtain information on the table from an external database or server via a network.

FIG. 6B shows the display reduced from that in FIG. 6A equally in the vertical and horizontal directions. However, the control unit 504 can perform display control by reducing the display in the display usage area 102 only in the vertical direction or horizontal direction depending on the sliding/moving direction of the monitor 8. If the X-ray tube 1 is not at the accommodation position, the control unit 504 may always perform display control for full display like that shown in FIG. 6A. This allows the operator to easily understand that the movement of the monitor 8 is limited to only when moving the apparatus.

With the above arrangement, sliding/moving the monitor 8 can implement display in the display usage area 102 at an optimal display position and in an optimal display size in accordance with the movement of the monitor 8. This allows the operator to visually check the entire monitor display information displayed in the display usage area 102, thereby improving the operability for the operator.

Figure 7A:
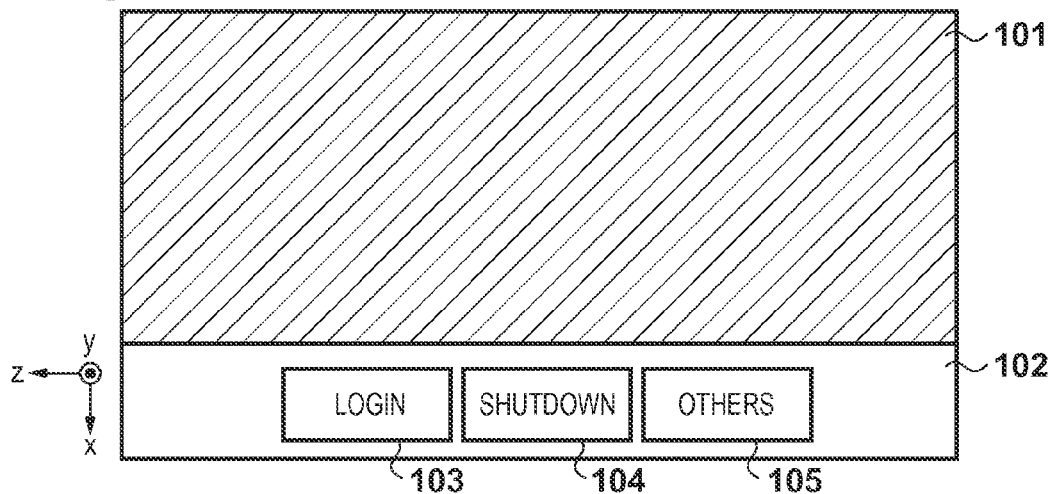
FIG. 7A is a view for explaining a monitor display before login operation at the time of the movement of the apparatus according to the second embodiment.

The control unit 504 may change the display contents on the monitor 8 based on an imaging procedure. Display contents on the monitor will be described with reference to FIGS. 7A and 8B. FIG. 7A exemplarily shows the display contents to be displayed when activating the apparatus and moving the apparatus. A logic button 103, a shutdown button 104 for shutting down the power supply of the apparatus, and an other settings button 105 to be used for selection other than login operation and shutdown operation are displayed in the display usage area 102 laid out on the lower side of the monitor 8. Laying out the display usage area 102 on the lower side of the monitor 8 can improve the visibility of the display usage area 102 for the operator. Note that the number and types of buttons displayed in the display usage area 102 are not limited to those in FIG. 7A. The number of selection buttons among other settings can be freely increased or decreased.

Figure 7B:
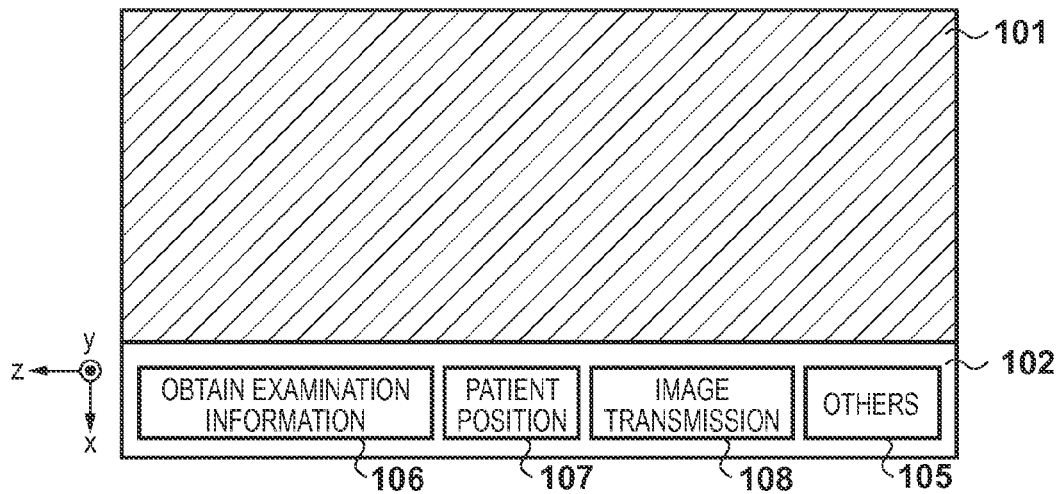
FIG. 7B is a view for explaining a monitor display after login operation at the time of the movement of the apparatus according to the second embodiment.

FIG. 7B exemplarily shows the display contents to be displayed during the movement of the apparatus after login operation. An examination information obtaining button 106 is a button for obtaining examination information by communicating with an intra-hospital network. A patient position button 107 is a button for seeing patient position information. Selecting the patient position button 107 will display a hospital map and hospital room information of an examination target patient (which will be referred to as "object position information"). An image transmission button 108 is a button for transmitting an image to an intra-hospital network. This button is used to transmit the image captured before selection. The examination information obtaining button 106, the patient position button 107, the image transmission button 108, and the other setting button 105 are displayed in the display usage area 102 laid out on the lower side of the monitor 8.

Figure 7C:
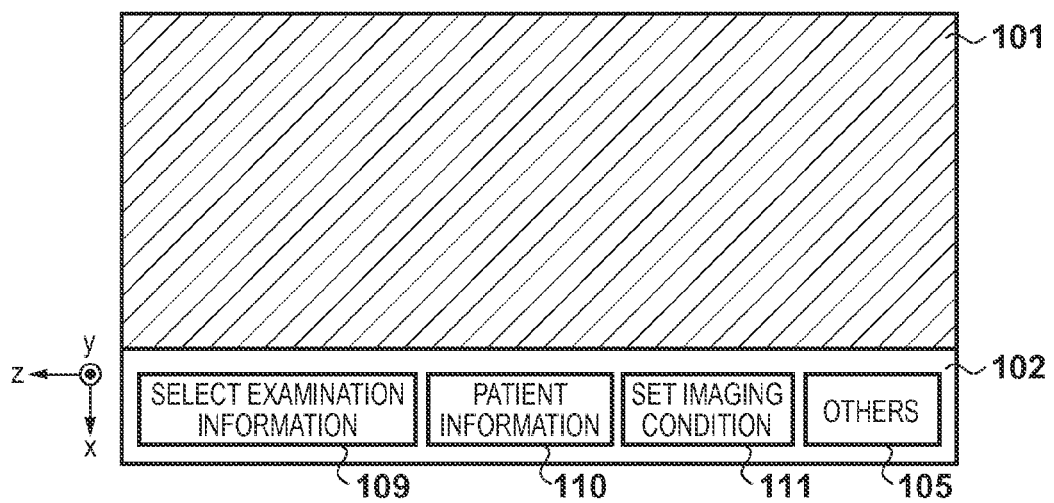
FIG. 7C is a view for explaining a monitor display at the completion of the movement of the apparatus according to the second embodiment.

FIG. 7C exemplarily shows the display contents to be displayed when the operator has moved the apparatus near an examination target patient. The apparatus includes the absolute position sensor 506 which detects, by using the position information of the object, that the cart unit 5 has approached a predetermined position relative to the object. The absolute position sensor 506 detects, by using the position information of the object, that the cart unit 5 has reached a predetermined position relative to the patient (object) on a hospital map. At this time, the control unit 504 may switch the display items from the display contents in FIG. 7B to the display contents in FIG. 7C. An examination information selection button 109 is a button for selecting an imaging region or imaging body posture based on the examination information list obtained by pressing the examination information obtaining button 106. A patient information button 110 is a button for checking the name, age, patient ID, and sex of a patient. An imaging condition setting button 111 is used to set, as imaging conditions, for example, a tube current, tube voltage, and X-ray irradiation time. The examination information selection button 109, the patient information button 110, the imaging condition setting button 111, and the other settings button 105 are displayed in the display usage area 102 laid out on the lower side of the monitor 8.

FIG. 8A exemplarily shows the display contents to be displayed when the operator has moved the X-ray tube 1 from the accommodation position. An area 112 is an area for displaying a captured image. An area 113 is an area for displaying the state of the X-ray sensor. This area displays an indication indicating that preparation is being made for imaging, the sensor is waiting for irradiation, or image data is being read, and indications indicating the stop state and the presence/absence and type of a grid. An area 114 is an area for displaying patient information. This area displays the name, age, patient ID, and sex of a patient. An area 115 is an imaging region selection area. An area 116 is an area for selecting an imaging direction for a patient. The display position and size of the display usage area 102 are switched to display the areas 112 to 116 in the entire monitor display enable range (display area).

FIG. 8B exemplarily shows the display contents to be displayed when the operator has returned the X-ray tube 1 to the accommodation position. Upon detecting that the X-ray tube 1 is accommodated at the accommodation position, the control unit 504 performs control to display contents in a partial display area on the monitor 8 (display unit). The control unit 504 reduces and displays the same contents as those in FIG. 8A in accordance with the sliding/moving amount of the monitor 8. In addition, the control unit 504 may change the display contents from those in FIG. 7A to those in FIG. 8B in accordance with selection by the operator so as to display an imaging procedure on the monitor 8 in the form of a list. The above display control by the control unit 504 can change the display contents in accordance with an imaging procedure, thereby further improving the operability for the operator.

Third Embodiment

Figure 9A:
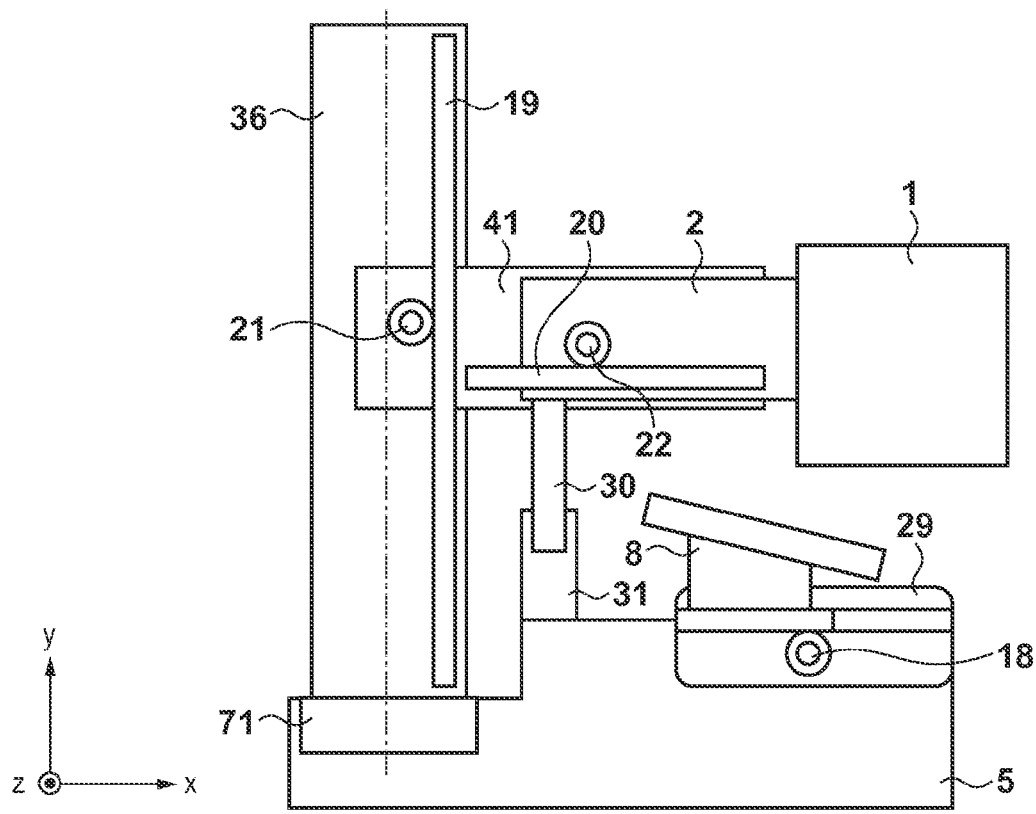
FIG. 9A is a view showing the arrangement of a radiation imaging apparatus according to the third embodiment.
Figure 9B:
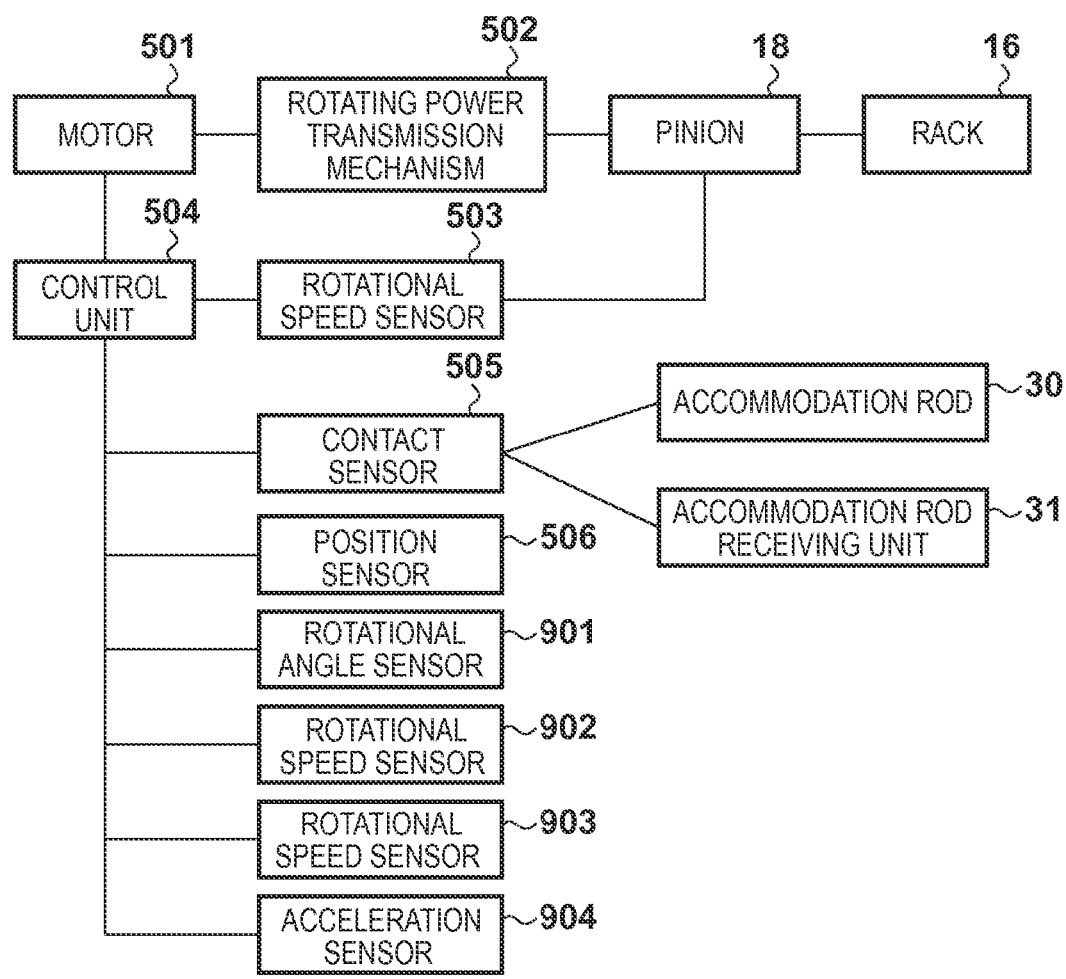
FIG. 9B is a block diagram showing the arrangement of the control system of the radiation imaging apparatus.

FIG. 9A shows the arrangement of a radiation imaging apparatus (movable X-ray imaging apparatus) according to the third embodiment. FIG. 9B shows the arrangement of the control unit and sensors of the movable X-ray imaging apparatus. The same reference numerals as those described above denote the same components in FIGS. 9A and 9B.

A column rotating unit 71 includes a rotational angle sensor 901 which detects the rotational angel of a column 36 relative to a cart unit 5. The detection result obtained by the rotational angle sensor 901 is input to a control unit 504. The column 36 is provided with a rack 19. A pinion 21 corresponding to the rack 19 is provided on a boom support unit 41. The pinion 21 is provided with a rotational speed sensor 902 which detects the rotational speed of the pinion 21.

The boom support unit 41 is provided with a rack 20. A pinion 22 corresponding to the rack 20 is provided on a boom 2. The pinion 22 is provided with a rotational speed sensor 903 which detects the rotational speed of the pinion 22. The detection results obtained by the rotational speed sensors 902 and 903 are input to the control unit 504.

The control unit 504 calculates the positions of the pinions 21 and 22 on the racks 19 and 20 from rotational speed detection results on the pinions 21 and 22. For example, when the operator moves the boom support unit 41 along the column 36, the pinion 21 provided in the boom support unit 41 rotates on the rack 19 provided on the column 36. The control unit 504 can calculate the position of the boom support unit 4 in the vertical direction (y direction) by using a rotational speed detection result on the pinion 21 and design values (for example, a pitch and a diameter) of the pinion 21. When the operator moves the boom 2 in the horizontal direction (x direction), the pinion 22 provided in the boom 2 rotates on the rack 20 provided in the boom support unit 41. The control unit 504 can calculate the position of the boom 2 in the horizontal direction (x direction) by using a rotational speed detection result on the pinion 22 and design values (for example, a pitch and a diameter) of the pinion 22.

The distal end portion of the boom 2 is connected to an X-ray tube 1. The control unit 504 can calculate the relative position between the X-ray tube 1 and the cart unit 5 from the rotational angle of the column rotating unit 71, and the calculation results of the position of a boom support unit 4 in the vertical direction and the position of the boom 2 in the horizontal direction.

FIG. 9A exemplarily shows the extension/contraction of the one-stage extension boom constituted by the boom 2 and the boom support unit 41. However, this boom may be a boom having a larger number of stages, and may have racks, pinions, and rotational speed sensors corresponding to the number of stages. In addition, in order to make the pinion stably rotate, a linear guide mechanism may be separately provided between the column 36 and the boom support unit 41 or between the boom support unit 41 and the boom 2.

With regard to other boom shapes, fixing the X-ray tube 1 at the accommodation position and providing an acceleration sensor 904 in the X-ray tube 1 allow the control unit 504 to calculate the moving amount of the X-ray tube 1 from the detection result obtained by the acceleration sensor 904.

In this case, the rotational angle sensor 901, the rotational speed sensors 902 and 903, and the acceleration sensor 904 function as a relative position detection unit for detecting the relative position between the X-ray tube 1 and the cart unit 5. This allows the control unit 504 to grasp the relative position between the X-ray tube 1 and the cart unit 5. With this operation, the control unit 504 obtains the position of the monitor 8 relative to the X-ray tube 1 from the relative position between the monitor 8 and the cart unit 5 described in the second embodiment and the relative position between the X-ray tube 1 and the cart unit 5 described above. Note that letting the X-ray tube 1 have a world coordinate detection sensor allows the control unit 504 to grasp the position of the X-ray tube 1.

The control unit 504 obtains the position of the monitor 8 relative to the X-ray tube 1 by using the relative position between the X-ray tube 1 and the cart unit 5 and the detection result obtained by the rotational speed sensor 503 (the position of the monitor 8 on the cart unit 5), and controls display on the monitor 8 in accordance with the relative position. The control unit 504 has a table associating the position of the monitor 8 relative to the X-ray tube 1 with the display area which can be visually checked by the operator. By using this table, the control unit 504 changes the display usage area 102 on the monitor 8 in accordance with a change in the position of the monitor 8 or a change in the position of the X-ray tube 1. The control unit 504 changes display (the display position and the display size) in the display usage area 102 of the monitor 8 by referring to the table in accordance with a change in the relative position of the monitor 8. Note that the control unit 504 can obtain information on the table indicating a relative positional relationship from an external database or server via a network.

With the above arrangement, when the operator moves the X-ray tube or the monitor, it is possible to implement optimal display on the monitor 8 in accordance with each movement. The operator can visually check the overall display information displayed on the monitor 8. This improves the operability for the operator.

Fourth Embodiment

FIGS. 11A and 11B show a radiation imaging apparatus (the arrangement of a movable X-ray imaging apparatus) according to the fourth embodiment. FIG. 11A is a plan view of the apparatus. FIG. 11B is a perspective view of the apparatus. In addition to the arrangement of the above embodiments, the movable X-ray imaging apparatus includes a wall 1113 (protection wall) for protecting against exposure, which covers at least part of an X-ray tube 1101 (irradiation unit) when it is accommodated at the accommodation position. Referring to FIGS. 11A and 11B, the X-ray tube 1101 irradiates radiation (X-rays). A collimator 1102 limits the X-ray irradiation range set on the X-ray tube 1101. A boom 1103 supports the X-ray tube 1101. The boom 1103 includes as extensible portion which moves the X-ray tube 1101 in at least the horizontal direction (x direction) and an extension/contraction position fixing portion. A column 1104 supports the boom 1103.

A boom support unit 1105 connects the boom 1103 to the column 1104, and includes a vertical moving portion which can move the boom 1103 in the vertical direction (y direction) along the column 1104 and a moving position fixing portion which can fix the boom 1103 at an arbitrary position on the column 1104 upon movement.

A cart unit 1106 supports the column 1104. The cart unit 1106 supports the X-ray tube 1101 through the boom 1103, the boom support unit 1105, and the column 1104. The cart unit 1106 can move while the X-ray tube 1101, the boom 1103, the boom support unit 1105, and the column 1104 are mounted on the unit.

A moving mechanism 1107 is a mechanism which allows the cart unit 1106 to move by rotating while, for example, a plurality of tires or casters are placed on a ground. A column rotating unit 1108 connects the cart unit 1106 to the column 1104 and includes a rotating member (for example, a bearing) at the connecting portion between the cart unit 1106 and the column 1104 to support the column 1104 on the cart unit 1106 so as to allow the column 1104 to rotate about an axis perpendicular to the ground. The column rotating unit 1108 also includes, for example, a non-excitation brake (rotational position holding unit), and can stop the rotation of the column 1104 at an arbitrary position by operating the non-excitation brake.

A monitor 1109 (display unit) is installed on the lower surface side of an accommodation unit for accommodating the X-ray tube 1101 at position where the monitor does not come into contact with the X-ray tube 1101 when the X-ray tube is accommodated. The monitor 1109 displays the information and location of a patient to be imaged at the time of doctor's round and an examination information list. The two opposite side surfaces of the monitor 1109 are supported so as to be slidable along monitor guide rails (not shown). This allows the monitor 1109 to slide/move back and forth in the direction indicated by the arrow in FIGS. 11A and 11B. In addition, the operator can perform operation to set imaging conditions and transmit a captured X-ray image to an intra-hospital network via the monitor 1109 (display unit). An accommodation rod receiving unit 1111 includes a contact sensor which detects that a lower surface 1110 or the boom 1103 has come into contact with or approached the accommodation rod receiving unit 1111.

Referring to FIGS. 11A and 11B, the lower surface 1110 of the boom 1103 need not be formed into a convex portion protruding from the boom 1103. For example, the accommodation rod receiving unit 1111 provided in the cart unit 1106, a magnet, and a magnetic sensor may detect that the boom 1103 or the X-ray tube 1101 is at the accommodation position at the time of the movement of the apparatus. The apparatus shown in FIGS. 11A and 11B can be configured to permit only two behaviors at the time of taking out the X-ray tube 1101, that is, the vertical movement of the column 1104 of the boom support unit 1105 and the rotation of the column 1104 upon releasing the brake of the column rotating unit 1108. Alternatively, the apparatus shown in FIGS. 11A and 11B may be configured to permit only the behavior of the vertical movement of the column 1104 of the boom support unit 1105 in the vertical direction at the time of taking out the X-ray tube 1101. The extension/contraction of the boom 1103 may be stopped by controlling the extension/contraction position fixing unit of the boom 1103. This further prevents the X-ray tube 1101 from coming into contact with the monitor 1109. In the apparatus shown in FIGS. 11A and 11B, the X-ray tube 1101 is accommodated on the monitor 1109, and the wall 1113 (protection wall) for protecting against exposure around the X-ray tube 1101 protrudes from the edge portion of the monitor 1109 at the time of the accommodation of the X-ray tube 1101. The wall 1113 (protection wall) for protecting against exposure has at least a height enough to cover the collimator 1102. This reduces the possibility that the collimator 1102 will receive an external impact at the time of accommodation, thereby contributing to a longer service life of the apparatus.

A control unit 504 (for example, FIG. 5B) of the apparatus has a rotational angle table storing data indicating the positional relationship between the X-ray tube 1101 and the exposure protection wall of the cart unit 1106 in a state in which they do not come into contact with each other. The control unit 504 can determine, by referring to the rotational angle table, whether the X-ray tube 1101 has approached the exposure protection wall 1113 (protection wall) of the cart unit 1106. This determination step may be added between steps S1020 and S1050 (for example, after X-ray tube position detection in step S1020) in the flowchart of FIG. 10. These operations prevent the X-ray tube 1101 from coming into contact with not only the monitor 1109 but also the exposure protection wall 1113 of the cart unit 1106.

Fifth Embodiment

FIGS. 12A and 12B show the arrangement of a radiation imaging apparatus (movable X-ray imaging apparatus) according to the fifth embodiment. FIG. 12A is a plan view of the apparatus. FIG. 12B is a perspective view of the apparatus. In addition to the arrangement of the above embodiments, the movable X-ray imaging apparatus of this embodiment includes a monitor 1109 and another monitor 1212 fixed to an X-ray tube 1101 (irradiation unit) through a collimator 1102. The same reference numerals as in FIGS. 12A and 12B denote the same components as those described with reference to FIGS. 11A and 11B, and a description of them will be omitted. In the case shown in FIGS. 12A and 12B, two walls 1113 (protection walls) for protecting against exposure protrude from a cart unit 1106 and extend to a position to cover a side surface of the collimator 1102 and at least part of the X-ray tube 1101. This reduces the possibility that the collimator 1102 and the X-ray tube 1101 will receive an external impact at the time of accommodation, thereby contributing to a longer service life of the apparatus.

In the case shown in FIGS. 12A and 12B, the apparatus includes the monitor 1212 (second monitor) belonging to the collimator 1102 in addition to the monitor 1109 (first monitor) placed on the cart unit 1106. As described with reference to FIGS. 11A and 11B, the monitor 1109 (first monitor) is configured to be slidable/movable in the direction indicated by the arrow in FIG. 12B. The monitor 1212 (second monitor) is configured as a so-called vari-angle display unit which can change the angle of a display screen. For example, the monitor 1212 (second monitor) is held by the collimator 1102 along one side of the display screen. It is possible to change the direction of the monitor 1212 (second monitor) around this side as an axis for angle change. The method of holding the monitor 1212 (second monitor) on the collimator 1102 is not limited to this. For example, the monitor 1212 (second monitor) an be configured to change its direction to an arbitrary direction within a predetermined angle range relative to the collimator 1102. In this case, the apparatus may further include an angle detection sensor which detects the angle of the monitor 1212 (second monitor).

As exemplarily shown in FIGS. 12A and 12B, when the X-ray tube 1101 and the collimator 1102 are accommodated, a control unit 504 (for example, FIG. 5B) turns on the power supply of the monitor 1212 (second monitor) while turning off the power supply of the monitor 1109 (first monitor). The control unit 504 can make the monitor 1212 (second monitor) display information necessary for the movement of the apparatus as described in the above embodiment. Instead of or in addition to this arrangement, the control unit 504 can make the slidable/movable monitor 1109 (first monitor) and the monitor 1212 (second monitor) display different pieces of information by performing display control.

For example, the control unit 504 can specify display usage areas with respect to the two monitors 1109 and 1212 by using a position detection result on the X-ray tube 1, a position detection result on the monitor 1109, and an angle detection result on the monitor 1212. In addition, the control unit 504 can control display contents in the display usage areas respectively specified for the two monitors 1109 and 1212. Effectively using the display usage areas on the two monitors 1109 and 1212 can further improve the convenience for the operator.

Sixth Embodiment

Figure 13:
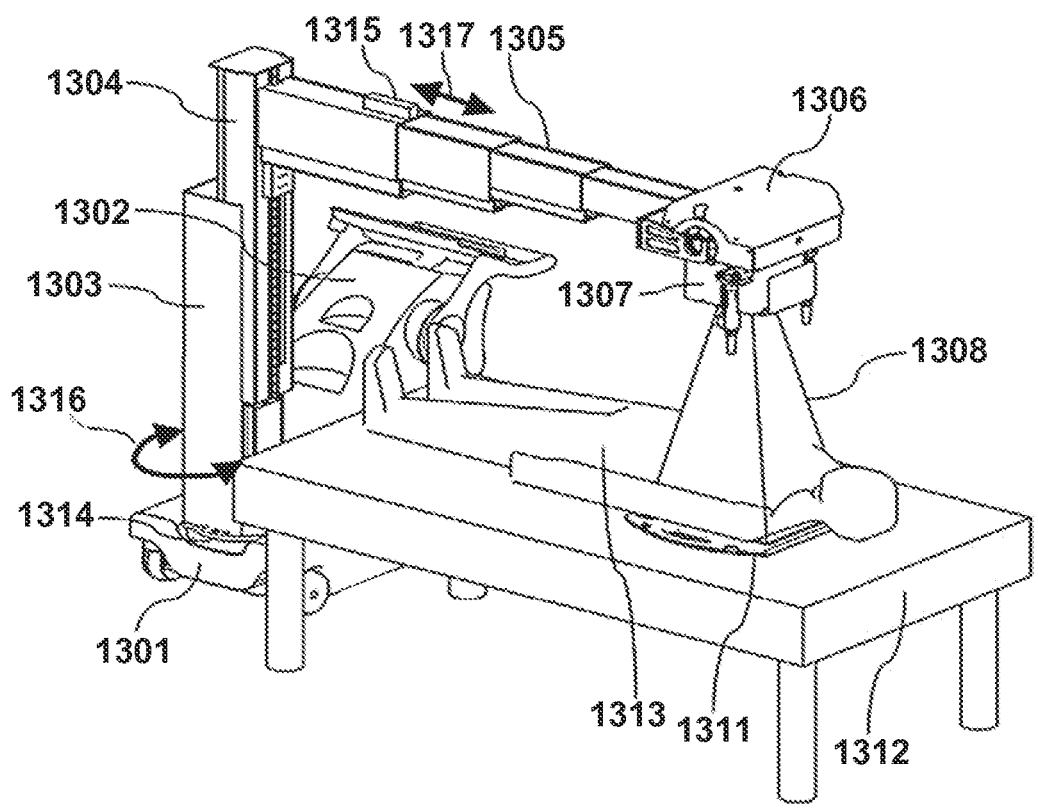
FIG. 13 is a perspective view showing the arrangement of a radiation imaging apparatus according to the sixth embodiment.

FIG. 13 shows the arrangement of a radiation imaging apparatus (movable X-ray imaging apparatus) according to the sixth embodiment. The movable X-ray imaging apparatus according to this embodiment includes a column (first and second columns 1303 and 1304) and an X-ray tube support boom 1305 (boom unit) as components of a positioning unit. The column extends and contracts in the first direction (the vertical direction relative to a moving cart 1301) and is coupled to the moving cart 1301 (cart unit). The X-ray tube support boom 1305 is configured such that an X-ray tube apparatus 1306 (irradiation unit) is coupled to one end side, while the other end side is supported by the column so as to be movable in the direction in which the column extends, and the boom can extend and contract in the second direction (horizontal direction 1317) crossing the first direction.

In the example of the arrangement shown in FIG. 13, the column which supports the X-ray tube support boom 1305 has a multi-stage structure. In addition, the X-ray tube support boom 1305 has a nesting or telescopic structure, and hence can extend and contract in accordance with operation by the operator. An X-ray control unit 1302 including an X-ray high voltage generator, an X-ray controller, and a control panel is mounted on the moving cart 1301. The X-ray control unit 1302 includes a handle for movement and a monitor (display unit) which can display X-ray irradiation information and input an irradiation command. The first column 1303 is vertically placed on the front side of the upper portion of the moving cart 1301 and can make a turn 1316 in all directions relative to the moving cart 1301. A pivotal displacement sensor 1314 detects the amount of turn of this column. The first column 1303 includes the second column 1304 which can vertically move along the column. If the apparatus is dedicated to a general hospital room and need not take any specific high position, the first column 1303 and the second column 1304 may be integrated into one column. In addition, this column is provided with the X-ray tube support boom 1305 which can contract in a horizontal direction 1317 which crosses the second column 1304 at an almost right angle. A displacement sensor 1315 detects the moving amount of the boom. The X-ray tube apparatus 1306 is attached to the distal end of the X-ray tube support boom 1305. A collimator 1307 is attached to the lower portion of the X-ray tube apparatus 1306. A flat panel 1311 for imaging is placed on a bed 1312 placed in a hospital room. The flat panel 1311 for imaging is placed between the bed 1312 and an object 1313 on the bed. The X-ray tube apparatus 1306 irradiates radiation (X-rays) 1308. The flat panel 1311 detects the radiation (X-rays) transmitted through the object 1313.

Note that one or both of the arrangements of the multi-stage column and extensible boom like those shown in FIG. 13 are not limited to this embodiment. For example, it is possible to use the arrangement of the movable radiation imaging apparatus described in each of the first to fifth embodiments, and the embodiment incorporates such modifications of the arrangement. Making the column and the boom have extensible multi-stage arrangements can have the effects of being compact at the time of accommodation, ensuring forward visibility, and facilitating handling.

Other Embodiments

Aspects of she present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application. No 2012-218460, filed Sep. 28, 2012, which is hereby incorporated by reference herein in its entirety.

What is claimed is:

1. A radiation imaging apparatus having an irradiation unit configured to irradiate radiation, a positioning unit configured to position said irradiation unit, and a cart unit configured to move while said irradiation unit and said positioning unit are mounted on said cart unit, said radiation imaging apparatus comprising:
    a moving unit configured to hold a display unit below said irradiation unit and to slide the display unit along with a display screen of the display unit;
    a detection unit configured to detect a position of the display unit; and
    a control unit configured to control display information on the display unit,
    wherein said control unit obtains the position detected by said detection unit and controls the display information on the display unit in accordance with the position.

2. The apparatus according to claim 1, wherein said control unit controls the display information on the display unit by referring to a table associating the position of the display unit with a display area used for display on the display unit.

3. The apparatus according to claim 1, wherein said control unit changes a position and display size of a display area of the display unit in accordance with the position of the display unit.

4. The apparatus according to claim 1, further comprising a relative position detection unit configured to detect a position of said irradiation unit relative to said cart unit,
    wherein said control unit obtains a relative position of the display unit relative to said irradiation unit by using a detection result obtained by said relative position detection unit and a detection result obtained by said detection unit, and controls display information on the display unit in accordance with the relative position.

5. The apparatus according to claim 4, wherein said control unit controls display information on the display unit by referring to a table associating a position of the display unit relative to said irradiation unit and a display area used for display on the display unit.

6. The apparatus according to claim 4, wherein said control unit changes a position and display size of a display area on the display unit in accordance with the relative position.

7. The apparatus according to claim 1, further comprising an accommodated state detection unit configured to detect that said positioning unit accommodates said irradiation unit at an accommodation position, at a time of movement of said cart unit,
wherein upon detecting that said irradiation unit is accommodated at an accommodation position, said control unit performs control to display content in a partial display area on the display unit.

8. The apparatus according to claim 7, wherein upon detecting that said irradiation unit is accommodated at an accommodation position, said control unit controls said moving unit so as to slide the display unit from an inside of an upper surface of said cart unit to an outside.

9. The apparatus according to claim 7, wherein upon detecting that said irradiation unit is accommodated at an accommodation position, said control unit releases a brake of said moving unit.

10. The apparatus according to claim 7, wherein when said accommodated state detection unit does not detect that said irradiation unit is accommodated at an accommodation position, said control unit performs control to display content in an entire display area of the display area.

11. The apparatus according to claim 7, wherein when said accommodated state detection unit does not detect that said irradiation unit is accommodated at an accommodation position, said control unit controls said moving unit so as to slide the display unit from an outside of an upper surface of said cart unit to an inside.

12. The apparatus according to claim 1, further comprising a position detection unit configured to detect, by using position information of an object, that said cart unit has approached a predetermined position relative to the object,
wherein said control unit switches display content on the display unit in accordance with a detection result obtained by said position detection unit.

13. The apparatus according to claim 1, further comprising a protection wall configured to cover at least part of said irradiation unit when said irradiation unit is accommodated at an accommodation position.

14. The apparatus according to claim 1, further comprising another display unit configured to be fixed to said irradiation unit.

15. The apparatus according to claim 1, wherein said positioning unit includes a column configured to extend and contract in a first direction and be coupled to said cart unit; and
a boom unit configured to have said irradiation unit coupled to one end side, be supported on the other end side so as to be movable in a direction in which said column extends, and extend and contract in a second direction crossing the first direction.

16. A method of controlling a radiation imaging apparatus having an irradiation unit configured to irradiate radiation, a positioning unit configured to position the irradiation unit, a cart unit configured to move while the irradiation unit and the positioning unit are mounted on the cart unit, and a moving unit configured to hold a display unit below the irradiation unit and slide the display unit along with a display screen of the display unit, the method comprising:
an obtaining step of obtaining a relative positional relationship between the irradiation unit and the display unit based on a state of the positioning unit and a state of the moving unit;
a specifying step of specifying a display area used for display on the display unit based on the positional relationship; and
a display control step of displaying information associated with radiation imaging in the specified display area.

17. A method of controlling a radiation imaging apparatus having an irradiation unit configured to irradiate radiation, a positioning unit configured to position the irradiation unit, and a cart unit configured to move while the irradiation unit and the positioning unit are mounted on the cart unit, the method comprising:
a moving step of holding a display unit below the irradiation unit and sliding the display unit along with a display screen of the display unit;
a detection step of detecting a position of the display unit; and
a control step of controlling display information on the display unit,
wherein the control step includes obtaining the position detected in the detection step and controlling the display information on the display unit in accordance with the position.

18. A radiation imaging apparatus having an irradiation unit configured to irradiate radiation, a positioning unit configured to position said irradiation unit, a cart unit configured to move while said irradiation unit and said positioning unit are mounted on said cart unit, and a moving unit configured to hold a display unit below said irradiation unit and to slide the display unit along with a display screen of the display unit, said radiation imaging apparatus comprising:
an obtaining unit configured to obtain a relative positional relationship between said irradiation unit and the display unit based on a state of said positioning unit and a state of said moving unit;
a specifying unit configured to specify a display area used for display on the display unit based on the positional relationship; and
a display control unit configured to display information associated with radiation imaging in the specified display area.

* * * * *